United States Patent [19]

Ranch et al.

[11] Patent Number: 5,008,200

[45] Date of Patent: Apr. 16, 1991

[54] PROPAGATING MULTIPLE WHOLE FERTILE PLANTS FROM IMMATURE LEGUMINOUS

[75] Inventors: Jerome P. Ranch; Julie A. Buchheim, both of Champaign, Ill.

[73] Assignee: United AgriSeeds, Inc., Savoy, Ill.

[21] Appl. No.: 197,355

[22] Filed: May 23, 1988

Related U.S. Application Data

[63] Continuation-in-part of Ser. No. 860,979, May 8, 1988, abandoned.

[51] Int. Cl.$^5$ .............................................. C12N 5/00
[52] U.S. Cl. ........................... 435/240.49; 435/240.48; 435/240.5; 435/240.54
[58] Field of Search ....................... 435/240.48, 240.49, 435/240.5, 240.54

[56] References Cited

U.S. PATENT DOCUMENTS 4,684,612 8/1987 Hemphill et al. ................ 435/240.5

OTHER PUBLICATIONS

Lippmann et al., 1984, Plant Cell Rep. 3: 215-218.
Lazzeri et al., 1985, Plant Mol. Biol. Rep. 3(4): 160-167.
Hammatt et al., 1987, J. Plant Physiol. 128 (3): 219-226.
Ammirato, P. 1983, pp. 100-104 In: Handbook of Plant Cell Culture, vol. 1, Evans et al., eds., MacMillan-New York.

*Primary Examiner*—Elizabeth C. Weimar
*Assistant Examiner*—David T. Fox

[57] ABSTRACT

Seeds of Glycine max, Glycine soja and hybrids thereof are produced by propagating embryogenic tissue containing multiple immature somatic embryos directly or serially by culturing particular cotyledonary tissue or derivation product thereof on media containing auxin selected from the group consisting of chloro-substituted phenoxyacetic acid, methyl derivative thereof, dicamba or picloram, incubating individual immature somatic embryos or embryogenic tissue containing such in a maturation stage to produce mature somatic embryos, germinating the mature somatic embryos to cause shoot tip formation, cultivating the germinated embryos to provide plantlets with 2 to 5 nodes and roots, cultivating the plantlets to provide whole fertile plants which flower and bear seeds, and recovering the seeds. Culturing to provide immature somatic embryos is carried out utilizing auxin in a concentration within the range of 2.5 to 1000 ppm effective to foster normal development of immature somatic embryos. 2,4-dichlorophenoxyacetic acid is the preferred auxin. Maturation is carried out in B5 or MS medium containing indolebutyric acid and abscissic acid or activated charcoal and sucrose, and germination is carried out in B5 or MS medium containing indolebutyric acid and gibberellic acid or MS medium containing filter sterilized L-proline and sucrose. Plantlet formation is carried out in B5 or MS medium without growth regulators. Plant and seed formation is carried out in soil or potting medium.

23 Claims, No Drawings

PROPAGATING MULTIPLE WHOLE FERTILE PLANTS FROM IMMATURE LEGUMINOUS

CROSS-REFERENCE TO RELATED APPLICATION

This application is a continuation-in part of the copending application Ser. No. 860,979, filed May 8, 1986, now abandoned.

TECHNICAL FIELD

This invention relates to a method of producing seeds for Glycine max (soybeans) or Glycine soja or hybrids thereof from relatively unorganized matter. This method relies on tissue culturing. This invention also relates to seeds and plants produced in the method.

BACKGROUND OF THE INVENTION

Regenerative techniques have heretofore been applied in respect to soybeans. For example, Beversdorf, W. D., et al., *Crop. Sci.*, 17:307-311 (1977) teaches culturing a soybean cell suspension to produce a meristematic center which does not resemble any stage of embryogenesis; and Christianson, M. L., et al., *Science*, 222:632-634 (1983) and U.S. Pat. No. 4,548,901 teach one case of generating a soybean plantlet from somatic embryo from axis from immature zygotic embryo but does not disclose that such plantlet was used to propagate a whole fertile plant.

None of the above are directed to propagating whole fertile plants from somatic embryos derived from embryogenic tissue from immature cotyledons. Moreover, none of these teach processing adaptable to isolating morphogenically competent protoplasts or to transforming embryogenic stem line or to selecting for resistance to anti-metabolites and other stresses or to culture associated genetic alterations, whereby unique whole fertile plants with useful new characteristics can be obtained and whereby seeds can be obtained from these plants for germination into plants.

SUMMARY OF THE INVENTION

It has been surprisingly discovered herein that immature tissue of Glycine max (soybeans), Glycine soja and hybrids thereof can be propagated into multiple whole fertile plants through a process of conversion to somatic embryos whereby whole fertile plants can be regenerated or genetically engineered. The whole fertile plants that are propagated are cultivated to bear seeds which can be marketed for crop use or planted to produce further generations of plants for seed production.

In particular, one embodiment of the invention herein involves a method of producing seeds from multiple whole fertile plants propagated from sterilized cotyledonary tissue of Glycine max or Glycine soja or hybrid thereof or from derivation product of said tissue.

The cotyledonary tissue useful in the method herein is in a particular stage of development, namely in the stage of development of cotyledons on a zygotic embryo which for Glycine max and hybrids are 4 to 8 mm in length and for Glycine soja are 1 to 4 mm in length. The cotyledonary tissue can be used in the form of whole zygotic embryo with cotyledons of the aforespecified length or in the form of cotyledons excised from said embryo.

The method herein comprises the steps of (a) propagating aseptic embryogenic tissue containing multiple immature somatic embryos directly or serially from said cotyledonary tissue or tissue derivation product thereof, said embryogenic tissue propagating comprising culturing cotyledonary tissue or derivation product thereof at a temperature ranging from 1° C. to 32° C. under a light intensity ranging from complete darkness up to 2400 lux in a semi-solid culturing medium composition containing growth regulator composition comprising a synthetic auxin selected from the group consisting of chloro-substituted phenoxyacetic aid, methyl derivative of chloro-substituted phenoxyacetic acid, dicamba, picloram, and mixtures thereof, said synthetic auxin being present at a concentration effective to foster normal development of multiple immature somatic embryos.

(b) incubating embryogenic tissue containing immature somatic embryos from step (a) or immature somatic embryos isolated therefrom to foster development of said immature somatic embryos into mature somatic embryos possessing well-formed cotyledons and radicle, (c) selecting mature somatic embryos from step (b) and germinating such to provide shoot tip formation, (d) cultivating the germinating somatic embryos from step (c) to provide plantlets comprising 2 to 5 nodes and roots, (e) cultivating the plantlets from step (d) to provide whole fertile plants, (f) cultivating a whole fertile plant from step (e) or a descendant thereof whereby it bears seeds, and (g) recovering the seeds.

DETAILED DESCRIPTION OF THE INVENTION

This invention has broad application to all genotypes of Glycine max, Glycine soja and hybrids thereof. The term "hybrids thereof" is used herein to mean hybrids within a species (e.g., hybrids of genotypes of Glycine max or hybrids of genotypes of Glycine soja) or hybrids between species (i.e., between a genotype of Glycine max and a genotype of Glycine soja).

Examples of genotypes of Glycine max subject to the method herein include Maple Arrow, Flambeau, McCall, Star, Jade, Ruby, A1492, A1937, Corsoy 79, Shawnee, Gem, A2575, Norsoy, B203, Onyx, Beeson 80, A3127, Topaz, Williams 82, Elf, Coker 355, AP350, Union Mitchell, Essex, A5474, Forrest, Bedford, FFR 560, Epps, Nathan, Arksoy, Bradley, and P.I. 404165. Examples of genotypes of Glycine soja subject to the method herein include P.I. 81762, P.I. 407222 and P.I. 407065. Examples of hybrids subject to the method herein include (B203 X A3127)$F_2$ and (Arksoy X G. soja P.I. 407222)$F_2$. P.I. is used herein as an abbreviation for plant introduction.

We turn now in detail to step (a) in the method described generally above.

The cotyledonary tissue for use in step (a) is obtained from seed pods of the genotype for which seeds are desired. The appropriate stage of development is readily determined by holding a seed pod under light so the silhouette of immature seed (zygotic embryo) within is visible. The seed pods selected for processing are those with silhouettes of length as previously specified for cotyledons since the length of the cotyledons in the embryo (each embryo contains two cotyledons) is essentially the same as the length of the embryo at this stage of development. Sterilized cotyledonary tissue is readily obtained from a seed pod by surface sterilizing the pod, e.g., by immersing in aqueous oxidizing agent such as aqueous sodium hypochlorite, hydrogen peroxide or bromine water, rinsing with sterile water, slicing the adaxial ridge of the pod, squeezing out the immature seed (zygotic embryo) and then sterilizing the immature seed, e.g., by immersing seeds utilizing a tea infuser in aqueous oxidizing agent and rinsing with sterile water. It is preferred to utilize a single cotyledon with its abaxial surface on the culture medium; this alternative is relatively simple and can be accomplished by excision of the cotyledon from the embryo to provide cotyledonary tissue, e.g., by utilizing a sterile scalpel to cut the embryo transversely to remove the cotyledons from the embryo axis.

Tissue derivation product of cotyledonary tissue can also be used to propagate embryogenic tissue containing multiple immature somatic embryos in step (a). Examples of derivation products of cotyledonary tissue useful in step (a) include (1) mature somatic embryo from step (b) in a prior execution of the process or core portion that produced said embryo, (2) germinated mature somatic embryo from step (c) in a prior execution of the process, (3) genetically engineered cotyledonary tissue prepared by wounding the tissue and inserting a new gene utilizing Agrobacterium vector, (4) cotyledonary tissue selected for resistance to antimetabolite or other stress, and (5) tissue derived from protoplasts obtained by chopping freshly excised cotyledonary tissue or cultured derivative thereof into segments and incubating the segments with cell degrading enzymes to release said protoplasts for transformation or somatic hybridization. Immature somatic embryos obtained from step (a) in a prior execution of the process are not suitable for use as derivation product of cotyledonary tissue in step (a). Processing to obtain the useful cotyledonary tissue derivation product is carried out aseptically.

Processing in step (a) and in steps (b)-(d) thereafter is carried out aseptically.

Culturing in step (a) is carried out at conditions of temperature and light which foster culturing. Use of temperatures below 1° C. can lead to freezing damage and use of temperatures above 32° C. can cause the tissue to die. Use of light intensity greater than 2400 lux causes the tissue to die. Preferably, culturing in step (a) is carried out at a temperature ranging from about 20° C. to about 28° C. at a light intensity ranging from about 50 lux to about 150 lux.

The culturing medium composition used in step (a) comprises culturing medium component and growth regulator composition component.

Culturing medium components useful for the culturing medium composition used in step (a) include all those media normally used for culturing plant regeneration in other species. The culturing medium components useful herein are aqueous compositions (the water constituent is deionized and distilled) and contain salts or acids as a source of nitrogen and minerals, vitamins and a carbon source. The salts or acids are typically classified as macronutrient furnishing (present, for example, at concentrations of 0.5-30 mM) and micronutrient furnishing (present, for example, at concentrations ranging from trace to 100 $\mu$m). Examples of macronutrient furnishing salts include ammonium nitrate, potassium nitrate, calcium chloride, magnesium sulfate, monobasic potassium phosphate, monobasic sodium phosphate, monobasic ammonium phosphate, ammonium phosphate, calcium nitrate, calcium chloride, and magnesium sulfate. Examples of micronutrient furnishing salts and acids include potassium iodide, boric acid, manganese sulfate, zinc sulfate, sodium molybdate, copper sulfate, cobalt chloride, and a source of iron, e.g., iron sulfate or iron-EDTA chelate. Typical vitamins include, for example, inositol (e.g., at a concentration of 500-10,000 $\mu$m), nicotinic acid (e.g., at a concentration of 4-45 $\mu$m), pyroxidine hydrochloride (e.g., at a concentration of 0.2-5 $\mu$m), thiamine hydrochloride (e.g., at a concentration of 0.2-30 $\mu$m) and glycine (e.g., at a concentration of 2-40 $\mu$m). The standard carbon source is sucrose at a concentration of 0.05-0.1M, especially at a concentration of 0.0875M. Suitable substitutes for sucrose include, for example, fructose, maltose or glucose at a concentration of 0.15-0.25M, e.g., 0.175M. Examples of very suitable culturing medium components for the culturing medium composition used in step (a) herein include MS (described in Murashige, T., et al, *Physiol. Plant.* 15, 473, 1962), B5 (described in Gamborg, O. L., *Exp. Cell Res.*, 50, 148, 1968), BL (described in Blaydes, D. F., *Physiol. Plant,* 19, 748-753, 1966), SH (described in Shenk, R. V., Can. J. Bot., 50, 199, 1972), WH (described in White, P. R., "The Cultivation of Animal and Plant Cells", 2d ed., Ronald Press, New York, 1963) and N6 (described in Chih-Ching, C., et al., *Scientia Sinica*, XVIII, No. 5, 659-668, Sept.-Oct., 1975). The media for step (a) include a gelling agent to provide the semi-solid state necessary. Suitable gelling agents include, for example, agar at a level of 0.6 to 0.8 percent, Gelrite at a level of 0.1 to 0.2 percent and agarose (pure basis) at a level of 0.2 to 0.4 percent.

The chloro-substituted phenoxyacetic acids useful for synthetic auxin constituent of the growth regulator composition component of the culture medium composition include, for example, 2,4-dichlorophenoxyacetic acid, 2,4,5-trichlorophenoxyacetic acid and para-chlorophenoxyacetic acid. The methyl derivative of chloro-substituted phenoxyacetic acid useful for synthetic auxin constituent includes, for example, 2-methyl-4-chlorophenoxyacetic acid. The preferred synthetic auxin constituent is 2,4-dichlorophenoxyacetic acid.

The concentrations of synthetic auxin constituents effective for culturing in step (a) depend on what other constituents are used in the growth regulating composition in the culture medium and, when serial propagation is used, in the pattern of concentrations in the various passages. If the concentration is too low, the somatic embryos produced are developmentally abnormal and cannot be converted into plants (normal and abnormal somatic embryos will be discussed later). If the concentration is too high the tissue being cultured turns brown and necrotic and dies. Generally, the concentration of synthetic auxins used ordinarily ranges from 2.5 to 1000 ppm. Normally, the concentration of synthetic auxins used ranges from 2.5 to 100 ppm, often from 20 to 40 ppm, and a very useful range when 2,4-dichlorophenoxyacetic acid is used as the sole synthetic in a direct propagation step, i.e., when step (a) consists of a single culturing, is 10 to 40 ppm. The combination of 2,4-dichlorophenoxyacetic acid (at a level of 2.5 ppm-10 ppm, especially 5 ppm) with 2,4,5-trichlorophenoxyacetic acid at these same concentrations also provides very suitable response when step (a) is a direct propagation step.

Synthetic auxins which are not useful except in combination with those mentioned above include indolebutyric acid and $\alpha$-naphthaleneacetic acid. When these are used both the concentration of the combination as well as the concentration of the required synthetic auxin should meet the above recited limits.

Activated charcoal is an optional growth regulator composition constituent. It is used for example at a concentration ranging from 0.25 to 0.75 percent by weight of the medium. When activated charcoal is used in conjunction with 2,4-dichlorophenoxyacetic acid, the 2,4-dichlorophenoxyacetic acid normally should be used at a level of 500-1000 ppm.

As indicated above step (a) can be carried out by propagating aseptic embryogenic tissue comprising multiple immature somatic embryos directly from cotyledonary tissue or from tissue derivation product of cotyledonary tissue without reculturing. By "immature somatic embryos" is meant that the embryos, when placed on conversion medium will germinate slowly (longer than about seven days), and/or will germinate at a low frequency (less than about 90%). In such case, step (a) is carried out over a 3 to 4 week period. However, carrying out step (a) serially has the advantage that the cultures from a single plant or group of plants can be preserved essentially indefinitely.

The serial propagation in step (a) comprises an initiation passage wherein embryogenesis is initiated and at least one subculturing passage. Each passage is typically 2 to 4 weeks, preferably 3 weeks. In each passage friable unorganized tissue (donated callus, i.e., unorganized group of cells formed in response to a cut, severing or injury of a plant or a plant part--see, for example ,column 3, lines 36 and 37 of Christianson et al., U.S. Pat. No. 4,548,901) forms in addition to organized tissue. It is important to separate the organized tissue from the unorganized tissue in a passage and to reculture only the organized tissue in the succeeding passage; otherwise the unorganized tissue grows so much faster than the organized tissue that it surrounds the organized tissue and hinders the development thereof. The friable unorganized tissue has an amorphous appearance with no regular surface and is tan to ivory in color, is somewhat translucent and has no visible supercellular organization. At operative auxin levels, the organized tissue comprises convoluted masses having smooth surfaces with a glassy opaque yellowish to pale green appearance. The separation of organized tissue from the unorganized tissue is readily carried out visually under a 7 to 12×dissection microscope.

Serial propagation can comprise, for example, performing an initiation passage on a semi-solid culturing medium composition containing growth regulating composition consisting of 2,4-dichlorophenoxyacetic acid in a concentration of from 20 to 40 ppm and performing each subculturing passage by aseptically transferring organized tissue after removal of friable unorganized tissue to fresh semi-solid culturing medium composition of the same composition as is used for the initiation passage.

Serial propagation can also comprise, for example, performing an initiation passage on a semi-solid culturing medium composition containing 2,4-dichlorophenoxyacetic acid used in a concentration ranging from about 2.5 ppm to about 10 ppm and each subculturing passage comprises aseptically transferring organized tissue after removal of friable unorganized tissue to fresh semi-solid culturing medium composition containing 2,4-dichlorophenoxyacetic acid in a concentration of from about 20 to about 100 ppm.

Serial propagation can also comprise, for example, utilizing a concentration of 2,4-dichlorophenoxyacetic acid in an initiation passage and subculturing passages alternating between a range of about 2.5 ppm to about 10 ppm and a range of about 40 ppm to about 100 ppm in successive passages.

The embryogenic tissue propagated in subculturing in serial propagation is deemed to comprise proembryonic cell stem line of the type described in Haccius, B., Phytomorphology, 28:74–81$x$ (1978).

During the course of step (a), about 2 weeks after step (a) is initiated, the cotyledons in the cotyledonary tissue becomes convoluted and covered with protrusions. Histological analysis of the tissue indicates meristematic areas. Cells contained therein are small, isodiametric, and highly spacially organized, and possess small to no vacuole, a granular cytoplasm, and a prominent heteropycnotic (dense in stain) nucleus. Protrusions upon histological examination are found to clearly be somatic embryos attached at their bases to the meristematic tissue.

The result of step (a) should be the production of embryogenic tissue containing normally developed immature somatic embryos, each about 0.5 to about 1.5 mm in length, colorless to pale green or yellow-green, translucent, spherical to ellipsoidal, resembling most closely a globular stage zygotic embryo; a photograph of normally developed immature somatic embryo is presented in FIG. 3 in Ranch, J. P., et al., In Vitro Cellular & Developmental Biology. Vol. 21, No. 11, pp. 653–658 (11/85). An abnormally developed somatic embryo, indicating improper conditions in step (a), is relatively large compared to normally developed somatic embryo (it is 2 mm or larger), of pronounced green color, opaque, trumpet shaped and occasionally fasciated.

We turn now to steps (b) and (c) in the method herein. In step (b) the immature somatic embryos from step (a) either isolated by dissection from the embryogenic tissue mass containing it or still as part of said tissue mass is subjected to a maturation medium to cause formation of mature somatic embryos. Any friable tissue is eliminated on transfer of tissue from step (a) to step (b). The mature somatic embryos formed in step (b) are each about 0.5-1 cm in length and pale green in color. If the immature somatic embryos are used in the form of the embryogenic tissue mass containing them, the formed mature somatic embryos are attached in rosette-like fashion at their bases to a core of morphogenically competent tissue; a photograph of such rosette-like structure is depicted in FIG. 5 of Ranch et al. cited above. As previously indicated either the rosette-like structure or core thereof can be used in step (a) in a process herein as derivation product of cotyledonary tissue for propagating embryogenic tissue containing multiple immature somatic embryos. In step (c) the matured somatic embryos from step (b) are selected and individually transferred to a germinating medium where shoot tips develop. In the case where a rosette-like structure is formed in step (b), the matured somatic embryos are cut from the rosette-like structure for the individual transfer to the germinating medium. The shoot tips are a darker green growth and contain trichomes; shoot tip development is shown in the photograph depicted in FIG. 4 of Ranch et al. cited above.

One method for carrying out steps (b) and (c) comprises for step (b) transferring isolated immature somatic embryos or embryogenic tissue containing immature somatic embryos to a semi-solid or liquid B5 or MS medium containing from about 0.25 μm to about 1 μm indolebutyric acid and from about 0.05 μm to about 5 1 μm abscissic acid, incubating at 1° C. to 32° C., preferably at 20° C. to 28° C., under low light (about 50 lux to about 150 lux) for about 7 to about 21 days, preferably for about 10 to about 14 days, until the immature somatic embryos develop into mature somatic embryos possessing well-formed cotyledons and radicle, and for step (c), selecting and individually transferring mature somatic embryos from step (b) to a semi-solid or liquid germination medium consisting essentially of B5 or MS medium containing from about 0.25 μm to about 1 μm indolebutyric acid and from about 0.1 μm to about 0.5 μm gibberellic acid at 1° C. to 32° C., preferably at about 20° C. to about 28° C., under low light (about 50 to about 150 lux) for about 2 to about 8 weeks until the shoot tips of the somatic embryos become evident. References to a description of B5 and MS media are set forth above. A semi-solid medium is used in steps (b) or (c) by adding gelling agents as described to provide semi-solid medium for step (a).

A second method for carrying out steps (b) and (c) comprises for step (b) transferring isolated immature somatic embryos or embryogenic tissue containing immature somatic embryos to semi-solid or liquid B5 or MS medium containing from about 0.1 percent to about 4 percent activated charcoal and from about 5 percent to about 20 percent sucrose and incubating at a temperature of from about 1° C. to about 32° C., preferably from about 20° C. to about 28° C., under low light (about 50 lux to about 150 lux) for about 7 to about 21 days, preferably for about 10 to about 14 days, to cause maturation of the somatic embryos, and for step (c) selecting and individually transferring mature somatic embryos from step (b) to a semi-solid or liquid germination medium consisting essentially of MS medium containing from about 20 to about 50 mM filter sterilized L-proline and from about 1 percent to about 5 percent sucrose and incubating at 1° C. to 32° C., preferably at about 20° C. to about 28° C., under low light (about 50° lux to about 150 lux) for about 7 to about 21 days, preferably about 10 to about 14 days until the shoot tips of the somatic embryos become evident. References to a description of B5 and MS media are set forth above. A semi-solid medium is used in steps (b) and (c) by adding gelling agent as described to provide semi-solid medium for step (a).

In steps (b) and (c), it is preferable to subculture to fresh medium of the same composition at 7 to 14 day intervals.

A third method and a fourth method for carrying out steps (b) and (c) provide immature somatic embryos having conversion vigor. By "converion vigor" is meant that immature somatic embryos subjected to the third or fourth method will germinate at a greater velocity and/or germinate in a greater percentage than somatic embryos not subjected to the third or fourth methods.

In the third method, step (b) comprises transferring isolated or embryogenic tissue containing immature somatic embryos to a semi-solid or liquid maturation medium. The maturation medium contains commonly used culturing components such as described on Page 7, line 4 to Page 10, line 2. The maturation medium comprises from about 0.6% to about 1% of agar, or about 0.1% to about 0.4% of an agar substitute such as Gelrite; and from about 6% to about 12%, preferably about 10%, sucrose. In a preferred embodiment, the maturation medium also contains activated charcoal in an amount of from about 0.1% to about 1%.

The immature somatic embryos or embryogenic tissue containing immature somatic embryos are incubated at a temperature of from about 15° C. to about 30° C., preferably from about 20° C. to about 28° C., and under a light intensity of from about 500 lux to about 2000 lux for a period of time sufficient to reduce the water content of substantially all of the somatic embryos by an amount effective to bring about an increased conversion frequency. By "increased conversion frequency" is meant that the frequency and rate of germination of the embryos is increased. The Applicants have found that substantially all of the somatic embryos should lie on the maturation media for a period of from between about 50 and 65 days, and preferably from about 55 and 60 days. During the desiccation period, the maturation medium tends to dehydrate, causing additional elevation of the osmolarity of the culture medium and causing further osmotic effects in addition to the influence of the sucrose already present. The somatic embryos are desiccated so that the water content of substantially each somatic embryo is reduced to about 60% or less of its total fresh weight.

For step (c), the third method comprises selecting and transferring mature somatic embryos from step (b) to a semi-solid or liquid germination medium consisting essentially of a conversion medium containing from about 0.6% to about 1% of agar, or about 0.1% to about 0.4% of an agar substitute such as Gelrite; and from about 1% to about 3% sucrose. While on the conversion medium, the mature somatic embryos are exposed at 20° C. to 30° C., under a flourescent light having an intensity of from about 2000 lux to about 4000 lux for a period of time until conversion occurs. Conversion is defined as the development of the root and shoot apex of the somatic embryos, regardless of the relative sizes of the apices. Conversion generally occurs in a period of from about 2 to about 21 days.

In a fourth method for carrying out steps (b) and (c), step (b) comprises transferring isolated immature somatic embryos or embryogenic tissue containing immature somatic embryos to a semi-solid or liquid maturation medium. The maturation medium contains commonly used culturing components such as described on Page 7, line 4 to Page 10, line 2. The maturation medium comprises from about 0.6% to about 1% of agar, or about 0.1% to about 0.4% of an agar substitute such as Gelrite: and from about 6% to about 12%, preferably about 10%, sucrose. In a preferred embodiment, the maturation medium also contains activated charcoal in an amount of from about 0.1% to about 1%.

The immature somatic embryos or embryogenic tissue containing immature somatic embryos is incubated at a temperature of from about 15° C. to about 30° C., preferably from about 20° C. to about 28° C. and under a light intensity of from about 500 lux to about 2000 lux for a period of from about 25 to about 50 days, preferably about 40 days. After incubation, the immature somatic embryos or embryogenic tissue containing immature somatic embryos are then subjected to an accelerated desiccation procedure.

One procedure for accelerating the desiccation the somatic embryos is to remove the embryos from the maturation medium and place them in a chamber in which the somatic embryos will be subjected to lowered relative humidity. Generally, the immature somatic embryos are subjected to a relative humidity of from between about 70% and about 95%, preferably from about 75% to about 80%. The somatic embryos are desiccated so that the water content of substantially each somatic embryo is reduced to about 60% or less of its total fresh weight. The length of time for which the immature somatic embryos should be desiccated will generally vary inversely with the relative humidity employed.

The somatic embryos may be subjected to the lowered relative humidity by placing them in a desiccation chamber for which a predetermined relative humidity is already established, or the somatic embryos may be placed in the chamber in which the relative humidity is gradually lowered. While in the desiccation chamber, the immature somatic embryos or embryogenic tissue containing immature somatic embryos, is exposed under a flourescent light having an intensity of from about 200 lux to about 500 lux, at a temperature of from about 20° C. to about 30° C.

Accelerated desiccation may be accomplished by any conventional means for reducing the water content within the somatic embryo. Such techniques are well-known to skilled artisans and may be practiced without undue experimentation. An exemplary technique is taught by L. A. Rosenberg et al. in the *J. Expt. Bot.*, Volume 37, pages 1663–1674, the teachings of which are hereby incorporated by reference.

In the various processing steps, indolebutyric acid, abscissic acid and gibberellic acid are preferably filter-sterilized for use.

We turn now to step (d) where the germinated somatic embryos from step (c) are transferred to a plantlet developing medium comprising B5 or MS medium free of phytohormones and incubating is carried out at a temperature ranging from 1° C. to 32° C., preferably from 20° C. to 28° C. under low light (about 50 lux to about 150 lux) for about 1 to about 4 weeks until the appropriate plantlets are formed. These have root structure and 2 to 5 nodes.

In steps (a)–(d) the media except for filter sterilized components are normally sterilized by autoclaving, e.g., utilizing 16 psi steam. The pH of the media prior to autoclaving normally ranges from 5.6 to 6.0.

In step (e) the plantlets from step (d) are planted in soil or potting medium, e.g., in a greenhouse or in the field and under ambient normal growth conditions develop into whole fertile plants. In step (f) these plants flower and develop seeds. In step (g) these seeds are recovered for sale or use for crops or to provide further generations of plants from which seeds can be recovered. Steps (e)–(g) are readily carried out by conventional plant husbandry techniques.

Seeds are recovered from the plants propagated in steps (a)–(e) herein or from descendants thereof by harvesting the seed pods and separating the seeds therefrom, for example, by hand or by using a thresher or combine.

The following examples illustrate preferred aspects of the invention.

EXAMPLE I

Developing seed pods of field grown Epps genotype of Glycine max (soybean) are examined in situ by holding them up to light so that the silhouettes of the immature seeds within the pods are denoted. Five hundred pods each containing 2 to 4 seeds 4–8 mm in length are chosen based on the silhouette length.

The pods are surface sterilized by immersion in 10 percent Clorox for 40 minutes and then are rinsed with 1000 ml of sterile distilled water to remove the Clorox. Then the pods are cut open with a scalpel and the immature seeds are dissected out and placed into 50 ml of a holding solution of sterile water.

The immature seeds are then placed in a tea infuser and are surface sterilized by immersion in 5 percent Clorox for 15 minutes and rinsed with 250 ml of sterile distilled water.

The immature seeds are then placed into a sterile petri dish and the immature zygotic embryos are dissected aseptically from the immature seeds. These zygotic embryos are light green translucent structures containing 2 ovoid cotyledons with an embryo axis 0.5–1 mm long. From the 500 pods about 1500 zygotic embryos are obtained.

The embryos with cotyledon side down are placed 10 each to a 60×20 mm petri dish containing 20 ml of semi-solid MS medium containing 3 percent sucrose and 30 ppm 2,4-dichlorophenoxyacetic acid and 0.8 percent agar and incubation is carried out at 28° C. with 100 lux illumination.

After incubation for 2 weeks, the margins of the cotyledons of the embryos develop convolutions. Upon these convolutions immature somatic embryos develop by 3 to 4 weeks. These are about 0.5 to about 1.5 mm in length, colorless to pale green or yellow green, translucent, spherical to ellipsoidal and resemble most closely globular stage zygotic embryos and are attached to masses of cotyledonary tissue.

Masses of tissue containing the immature somatic embryos are aseptically transferred to semi-solid sterilized MS medium containing 0.5 percent activated charcoal, 10 percent sucrose and 0.8 percent agar for maturation. Each tissue mass is transferred to 20 ml of the medium in a 60×20 mm petri dish. Friable tissue is eliminated prior to the transfer. Incubation is carried out for 14 days at 28° C. at continuous 100 lux with subculturing to fresh medium on the eighth day. The somatic embryos mature into 0.5 to 1 cm long pale green opaque structures with well formed cotyledons. These resemble most closely mature zygotic embryos. The mature somatic embryos are present in groups attached in rosette fashion to a core portion.

The mature somatic embryos are dissected from the rosette-like group and are individually transferred to semi-solid sterile MS medium containing 3 percent sucrose, 50 mM filter-sterilized L-proline and 0.8 percent agar with no phytohormones for germination. The embryos are positioned in 20 ml medium in a 60×20 mm petri dish, 10 embryos to a petri dish. Embryos are positioned such that radicle and cotyledon are in contact with culture medium. Incubation is carried out at 28° C. under continuous 100 lux with subculturing to fresh medium on the 15th day. In 4 weeks, the embryos germinate by developing shoot tips.

The embryos with developed shoot tips are each transferred to a 25×125 mm test tube containing 15 ml of a sterilized MS medium with 0.8 percent agar and with no phytohormones. Incubating is carried out at 28° C. under continuous 100 lux to provide plantlets. Plantlets develop 3 nodes and roots within 7 to 21 days after initiation of incubation.

When this occurs, the plantlets are transferred to soil in a greenhouse at 85° F. They are covered with plastic bags and are uncovered for 2 to 4 hours at two day intervals for 2 weeks. They are then uncovered and are exposed to a 16 hour light (with light supplementation from mercury vapor lamps) 8 hour dark photo period. In 2 to 5 months, the plantlets develop into whole fertile plants which flower and set seed and the seeds mature into viable seeds. The viable seeds are harvested from the propagated plants and are planted to produce a subsequent generation which in turn provides seeds for planting.

Use of individual immature somatic embryos dissected from the masses of tissue containing them in place of the whole masses in Example I provides essentially the same results.

Use of liquid medium instead of semi-solid medium, i.e., use of medium without the agar, in steps (b) and (c) provides essentially the same results.

Use of B5 medium instead of MS medium in culturing to form immature somatic embryos, and in the maturation stage, and in plantlet forming provides essentially the same results.

Substitution of other genotypes for the Epps genotype used herein, e.g., use of Union, Star, Corsoy 79, Maple Arrow, Essex, McCall, Jade, Shawnee, Mitchell, Gem, AP350, A3127, Ruby, Flambeau, Arksoy, (Arksoy X G. soja P.I. 407222)$F_2$, G. Soja P.I. 407222, G. soja P.I. 81762, G. soja P.I. 407065, P.I. 404165 and (B203 X A3127)$F_2$ genotypes in place of Epps genotype above gives whole fertile plants bearing seeds which are recovered.

Use of 30 ppm of 2,4,5-trichlorophenoxyacetic acid or para-chlorophenoxyacetic acid or 2-methyl-4-chlorophenoxyacetic acid or picloram or dicamba or 5 ppm 2,4-dichlorophenoxyacetic acid in combination with 5 ppm 2,4-5-trichlorophenoxyacetic acid or 10 ppm 2,4-dichlorophenoxyacetic acid used with 10 ppm indolebutyric acid or with 10 ppm α-naphthaleneacetic acid, or 0.5 percent activated charcoal used with 640 ppm 2,4-dichlorophenoxyacetic acid in place of the 30 ppm 2,4-dichlorophenoxyacetic acid used above gives whole fertile plants bearing seeds which are recovered.

EXAMPLE II

This example is carried out the same as Example I except that mature somatic embryo produced in Example I is used in place of the zygotic embryos. Whole fertile plants bearing seeds are propagated and the seeds are recovered. The same results occur when core portion of rosette-like complex is used instead of mature somatic embryo.

EXAMPLE III

This example is carried out the same as Example I except that the cotyledons are dissected from the whole zygotic embryo and cultured instead of the whole embryo. Whole fertile plants bearing seeds are propagated and the seeds are recovered.

EXAMPLE IV

Tissue produced by incubating for 3 weeks on semi-solid MS medium containing 3 percent sucrose, 0.8 percent agar and 30 ppm 2,4-dichlorophenoxyacetic acid as in Example I is transferred to fresh medium of the same composition for a subculturing passage where culturing is carried out for 3 weeks at 28° C. under continuous 100 lux. Subculturing passages are carried out under these same conditions for a whole year. Friable unorganized tissue is removed prior to each subculturing, i.e., only organized material is subcultured. After one year of successive subculturing passages, masses of tissue containing immature somatic embryos are processed the same as these structures are processed in Example 1. Whole fertile plants bearing seeds are propagated and the seeds are recovered.

When processing is carried out as above except that in the initiation passage the culture medium contains 2,4-dichlorophenoxyacetic acid in a concentration of 5 ppm and in each subculturing passage the culture medium contains 2,4-dichlorophenoxyacetic acid in a concentration of 50 ppm, essentially the same results are obtained.

When processing is carried out as above except that the concentration of 2,4-dichlorophenoxyacetic acid alternates between 5 ppm and 50 ppm in successive passages, essentially the same results are obtained.

EXAMPLE V

Masses of tissue bearing immature somatic embryos are produced as in Example 1. One gram of the tissue is transferred to 20 ml liquid B5 medium in a 100×25 mm petri dish containing 0.6 μm indolebutyric acid and 0.6 μm abscissic acid. Incubation under continuous 100 lux and 28° C. with gyratory shaking at 40 rpm and reculturing to fresh medium on the eighth day gives mature embryos in 14 days. The mature embryos are dissected from rosette-like structure and are individually transferred to semi-solid B5 medium containing 0.8 percent agar, 0.6 μm indolebutyric acid and 0.3 μm gibberellic acid. Twenty ml of medium is used in a 60×20 mm petri dish. Incubation is carried out at 28° C. under continuous 100 lux with subculturing to fresh medium at 14 day intervals. After development of apical area in 2 to 8 weeks, the germinated somatic embryos (with shoot tips) are each transferred to 25×125 mm test tube containing 15 ml of sterilized MS medium with 0.8 percent agar and no phytohormones. Incubating is carried out at 28° C. under continuous 100 lux to provide plantlets. When the plantlets have 3 nodes and roots, they are transferred to soil in a greenhouse at ambient conditions and develop into whole fertile plants which flower and bear seeds. Seeds are harvested from the propagated plants and are planted to produce a subsequent generation which in turn provides seeds for planting.

EXAMPLE VI

Masses of immature somatic embryos are produced as in Example 1. The immature somatic embryos are dissected from the cotyledonary surface and are aseptically transferred individually, or in clumps of 2-8 embryos, to a semi-solid sterilized MS medium containing 10% sucrose, 0.5% activated charcoal, and 0.8% agar for maturation. Approximately 50 embryos are cultured per 60×20 mm Petri dish. The Petri dishes are left unsealed in a plastic box at 28° C. under 1000 lux from cool-white light fluorescent lamps for a 24 hour photoperiod of 16 hours continuous light per 8 hours continuous darkness.

After about 8 weeks, the somatic embryos are transferred to a semi-solid SH medium containing about 1% sucrose and 0.2% Gelrite. The somatic embryos are cultured 10 per 100×25 mm Petri dish. The somatic embryos are subjected, at a temperature of 28° C., to a photoperiod of 16 hours under 3000 lux from cool-white light fluorescent lamps. The somatic embryos converted at a relatively high frequency and with relatively great vigor.

The embryos with developed shoot tips are transferred to a 25×125 mm test tube containing 15 ml of a sterilized SH medium with 0.8% agar and with no phytohormones. Incubation is carried out at a temperature of about 28° C. under continuous 100 lux to provide plantlets. Plantlets develop 3 nodes and roots within 7 to 21 days after initiation of incubation.

When this occurs, the plantlets are transferred to a 5 gallon pot containing standard greenhouse potting mix, and are covered with transparent 20 oz. plastic cups for acclimatization.

EXAMPLE VII

Developing seed pods of field grown Gem genotype of Glycine max L. are examined in situ by holding them up to light so that the silhouettes of the immature seeds within the pods are denoted. Five hundred pods each containing 2 to 4 seeds 3-5 mm in length are chosen based on silhouette length, the pods are generally from about 15 to about 21 days post flowering.

The pods are surface sterilized by immersion in 10% Clorox for 40 minutes and then are rinsed with 100 ml of sterile distilled water to remove the Clorox. The pods are cut open with a scalpel and the immature seeds are shelled and placed into 50 ml. of a holding solution of sterile water.

The immature seeds are placed in a tea infuser and are surface sterilized by immersion in 5% Clorox for 15 minutes and rinsed with 250 ml of sterile distilled water.

The immature seeds are placed into a sterile petri dish and the immature zygotic embryos are dissected aseptically from the immature seeds. These zygotic embryos are light green translucent structures containing two ovoid cotyledons with an embryo axis 0.5-1 mm long. From the 500 pods about 1500 zygotic embryos are obtained. (The embryos with cotyledon side down are placed 10 each to a 60×20 mm petri dish containing a semisolid of MS medium containing 3% sucrose and 87 $\mu$M 2,4dichlorophenoxyacetic acid and 0.8% agar and incubation is carried out at a temperature of 28° C., and under continuous illumination at 20 lux.

After incubation for 30 days, the margins of the cotyledons of the embryos develop convolutions. Upon these convolutions immature somatic embryos develop by 3 to 4 weeks. These are about 0.5 to about 1.5 mm in length, colorless to pale green or yellow green, translucent, spherical to ellipsoidal, and resemble most closely globular stage zygotic embryos; and are attached to masses of cotyledonary tissue.

The immature somatic embryos are dissected from the cotyledonary surface and, for maturation, are aseptically transferred individually or in clumps of 2-8 embryos, to a semi-solid sterilized MS medium containing 10% sucrose, 0.5% activated charcoal, and 0.8% agar. Approximately 50 embryos are cultured per 0×20 mm Petri dish. The Petri dishes are left unsealed in a plastic box. The somatic embryos are subjected to a photoperiod at 28° C. of 16 hours, and at a light intensity of 3000 lux.

After 40 days on the maturation media, the somatic embryos are placed 20 each on a sterile, dry 60×20 Petri dish and immediately transferred into a sealed plexiglass vessel containing $H_2SO_4$ in concentrations which provide about 75% and about 93% relative humidity, as set forth by ME Solomon, Bull. Entomol. Res., Volume 42, pages 543-554. The ratio of the volume of acid in the container to total container volume is about 1:2; the proper $H_2SO_4$ concentration for each humidity is determined by measuring the specific gravity of each dilution with a hydrometer. The somatic embryos are treated for 4 and 7 days, under the relative humidities set forth above; at a temperature of about 25° C.; and under fluorescent light emitting 500 lux.

After desiccation, the somatic embryos are rehydrated with sterile, distilled water for one hour. The embryos are then transferred to a semi-solid SH media containing 1% sucrose and 0.2% Gelrite. The somatic embryos are converted at a relatively high frequency and with relatively great vigor.

The embryos with developed shoot tips are each transferred to a 25×125 mm test tube containing 15 ml of a sterilized MS medium with 0.8% agar and with no phytohormones. Incubation is carried out at a temperature of about 28° C. under continuous 100 lux to provide plantlets. Plantlets develop 3 nodes and roots within 7 to 21 days after initiation of incubation.

When this occurs, the plantlets are transferred to a 5 gallon pot containing standard greenhouse potting mix, and covered with transparent 20 oz. plastic cups for acclimatization.

Other variations will be evident to those skilled in the art. Therefore, the scope of the invention is intended to be defined by the claims.

What is claimed is:

1. A method of producing seeds from multiple whole fertile plants, said method comprising the steps of:
   (a) culturing aseptic cotyledonary tissue on a culturing media to form immature somatic embryos, said aseptic cotyledonary tissue being of Glycine max or Glycine soja or hybrid thereof, in the form of whole zygotic embryo with cotyledons 4 to 8 in length for Glycine max or hybrid and 1 to 4 mm in length for Glycine soja or in the form of cotyledons excised from said embryo or from derivation product of said cotyledonary tissue, said culture media comprising a synthetic auxin in a concentration of from about 20 to about 40 ppm, said synthetic auxin being selected from the group consisting of 2,4,5-trichlorophenoxyacetic acid, para-chlorophenoxyacetic acid, 2-methyl-4-chlorophenoxyacetic acid, and 2,4-dichlorophenoxyacetic acid; and
   (b) incubating the immature somatic embryo isolated from a step (a) on a maturation medium for a length of time sufficient to reduce the water content of the somatic embryo by an amount effective to bring about an increased conversion vigor, said maturation medium comprising 6% to about 12% sucrose to foster development of the immature somatic embryos into mature somatic embryos possessing well-formed cotyledons and radicle.

2. The method of claim 1, wherein the immature somatic embryo is desiccated so that the water content of the somatic embryo is reduced to about 60% or less of its total fresh weight.

3. The method of claim 1, wherein the embryogenic tissue containing immature somatic embryos or immature somatic embryos are incubated at a temperature of from about between about 15° C. and about 30° C.

4. The method of claim 1, wherein the maturation medium further comprises activated charcoal in an amount of from about 0.1% to about 1% activated charcoal.

5. The method of claim 1, further comprising the following steps:
   (c) selecting mature somatic embryos from step (b) and germinating such mature somatic embryos to provide shoot tip formation, whereby germination is effected by culturing the mature somatic embryos at a temperature of between about 15° C. and about 30° C. in a semi-solid culturing medium containing from about 1% to about 3% sucrose;

(d) cultivating the germinated somatic embryos from step (c) to provide plantlets comprising 2 to 5 nodes and roots;

(e) cultivating the plantlets from step (d) to provide whole fertile plants;

(f) cultivating a whole fertile plant from step (e) or a descendant thereof whereby it bears seeds; and (g) recovering the seeds.

6. The method of claim 1 wherein the embryogenic tissue containing immature somatic embryo or immature somatic embryo isolated therefrom which is provided in step (a) is derived as follows:

propagating aseptic embryogenic tissue containing multiple immature somatic embryos directly or serially from said cotyledonary tissue or derivation product thereof, said embryogenic tissue propagating comprising culturing cotyledonary tissue or derivation product thereof in a semi-solid culturing medium composition containing growth regulator composition comprising a synthetic auxin selected from the group consisting of chloro-substituted phenoxyacetic acid, methyl derivative of chloro-substituted phenoxyacetic acid, dicamba, picloram, and mixtures thereof, said synthetic auxin being present in a concentration effective to foster normal development of multiple immature somatic embryos.

7. The method of claim 1 wherein said Glycine max is of a genotype selected from the group consisting of Maple Arrow, Flambeau, McCall, Star, Jade, Ruby, A1492, A1937, Corsoy 79, Shawnee, Gem, A2575, Norsoy, B203, Onyx, Beeson 80, A3127, Topaz, Williams 82, Elf, Coker 355, AP350, Union, Mitchell, Essex, A5474, Forrest, Bedford, FFR 560, Epps, Nathan, Arksoy, Bradley, and P.I. 404165; wherein said Glycine soja is of a genotype selected from the group consisting of P.I. 81762, P.I. 407222 and P.I. 407065; and wherein said hybrid is of a genotype selected from the group consisting of (B203 X A3127)$F_2$ and (Arksoy X G. soja P.I. 407222)$F_2$.

8. A method of producing seeds from multiple whole fertile plants, said method comprising the steps of:

(a) culturing aseptic cotyledonary tissue on a culturing media to form immature somatic embryos, said aseptic cotyledonary tissue being of Glycine max or Glycine soja or hybrid thereof, in the form of whole zygotic embryo with cotyledons 4 to 8 mm in length for Glycine max or hybrid and 1 to 4 mm in length for Glycine soja or in the form of cotyledons excised from said embryo or from derivation product of said cotyledonary tissue, said culture media comprising a synthetic auxin in a concentration of from about 20 to about 40 ppm, said synthetic auxin being selected from the group consisting
2,4,5-trichlorophenoxyacetic acid,
para-chlorophenoxyacetic acid,
2-methyl-4-chlorophenoxyacetic acid, and
2,4-dichlorophenoxyacetic acid;

(b) fostering development of the immature somatic embryo into a mature somatic embryo possessing well-formed cotyledons and radicle by the following steps:

(i) incubating the immature somatic embryo isolated from step (a) on a maturation medium containing from about 6% to about 12% sucrose for a length of time of from about 30 to about 50 days; and (ii) placing the or immature somatic embryo isolated from step (b) (i) into a desiccation chamber at a relative humidity of from about 70% to about 95% for a period of time effective to bring about an increased conversion vigor.

9. The method of claim 8, wherein the immature somatic embryo is desiccated so that the water content of the somatic embryo is reduced to about 60% or less of its total fresh weight.

10. The method of claim 8, wherein the maturation medium further comprises activated charcoal in an amount of from about 0.1% to about 1% activated charcoal.

11. A method of producing seeds from multiple whole fertile plants, said method comprising the steps of:

(a) culturing aseptic cotyledonary tissue containing at least one immature somatic embryo or at least one immature somatic embryo isolated therefrom on a culturing media to form immature somatic embryos, said aseptic cotyledonary tissue being of Glycine max or Glycine soja or hybrid thereof, in the form of whole zygotic embryo with cotyledons 4 to 8 mm in length for Glycine max or hybrid and 1 to 4 mm in length for Glycine soja or in the form of cotyledons excised from said embryo or from derivation product of said cotyledonary tissue, said culture media comprising a synthetic auxin in a concentration of from about 20 to about 40 ppm, said synthetic auxin being selected from the group consisting of 2,4,5-trichlorophenoxyacetic acid, para-chlorophenoxyacetic acid, 2-methyl-4-chlorophenoxyacetic acid, and 2,4-dichlorophenoxyacetic acid;

(b) fostering development of the immature somatic embryo into a mature somatic embryo possessing well-formed cotyledons and radicle by the following steps:

(i) incubating the aseptic cotyledonary tissue or immature somatic embryo isolated therefrom from step (a) on a maturation medium containing from about 6% to about 12% sucrose for a period of from about 50 to about 65 days.

12. The method of claim 8, wherein the embryogenic tissue containing at least one immature somatic embryo or at least one immature somatic embryo isolated therefrom is incubated at a temperature of from about between about 15° C. and about 30° C.

13. The method of claim 8, wherein the immature somatic embryo is cultured, in step (b) (ii), at a relative humidity of between 75% and about 80%.

14. The method of claim 8, further comprising the following steps:

(c) selecting mature somatic embryos from step (b) and germinating such mature somatic embryos to provide shoot tip formation, whereby germination is effected by culturing the mature somatic embryos at a temperature of between about 15° C. and about 30° C. in a semi-solid culturing medium containing from about 1% to about 3% sucrose;

(d) cultivating the germinated somatic embryos from step (c) to provide plantlets comprising 2 to 5 nodes and roots;

(e) cultivating the plantlets from step (d) to provide whole fertile plants;

(f) cultivating a whole fertile plant from step (e) or a descendant thereof whereby it bears seeds; and (g) recovering the seeds.

15. The method of claim 8 wherein the embryogenic tissue containing at least one immature somatic embryo or at least one immature somatic embryo isolated therefrom which is provided in step (a) is derived as follows:

propagating aseptic embryogenic tissue containing multiple immature somatic embryos directly or serially from said cotyledonary tissue or derivation product thereof, said embryogenic tissue propagating comprising culturing cotyledonary tissue or derivation product thereof in a semi-solid culturing medium composition containing growth regulator composition comprising a synthetic auxin selected from the group consisting of chloro-substituted phenoxyacetic acid, methyl derivative of chloro-substituted phenoxyacetic acid, dicamba, picloram, and mixtures thereof, said synthetic auxin being present in a concentration effective to foster normal development of multiple immature somatic embryos.

16. The method of claim 8 wherein said Glycine max is of a genotype selected from the group consisting of Maple Arrow, Flambeau, McCall, Star, Jade, Ruby, A1492, A1937, Corsoy 79, Shawnee, Gem, A2575, Norsoy, B203, Onyx, Beeson 80, A3127, Topaz, Williams 82, Elf, Coker 355, AP350, Union, Mitchell, Essex, A5474, Forrest, Bedford, FFR 560, Epps, Nathan, Arksoy, Bradley, and P.I. 404165; wherein said Glycine soja is of a genotype selected from the group consisting of P.I. 81762, P.I. 407222 and P.I. 407065; and wherein said hybrid is of a genotype selected from the group consisting of (B203 X A3127)$F_2$ and (Arksoy X G. soja P.I. 407222)$F_2$.

17. A method of producing seeds from multiple whole fertile plants, said method comprising the steps of:

(a) culturing aseptic cotyledonary tissue on a culturing media to form immature somatic embryos, said aseptic cotyledonary tissue being of Glycine max or Glycine soja or hybrid thereof, in the form of whole zygotic embryo with cotyledons 4 to 8 mm in length for Glycine max or hybrid and 1 to 4 in length for Glycine soja or in the form of cotyledons excised from said embryo or from derivation product of said cotyledonary tissue, said culture media comprising 2,4-dichlorophenoxyacetic acid in a concentration of from about 10 to about 40 ppm; and (b) incubating the immature somatic embryo isolated from step (a) on a maturation medium for a length of time sufficient to reduce the water content of the somatic embryo by an amount effective to bring about an increased conversion vigor, said maturation medium comprising 6% to about 12% sucrose to foster development of said the immature somatic embryos into mature somatic embryos possessing well-formed cotyledons and radicle.

18. A method of producing seeds from multiple whole fertile plants, said method comprising the steps of:

(a) culturing aseptic cotyledonary tissue on a culturing media to form immature somatic embryos, said aseptic cotyledonary tissue being of Glycine max or Glycine soja or hybrid thereof, in the form of whole zygotic embryo with cotyledons 4 to 8 mm in length for Glycine max or hybrid and 1 to 4 mm in length for Glycine soja or in the form of cotyledons excised from said embryo or from derivation product of said cotyledonary tissue, said culture media comprising 2,4-dichlorophenoxyacetic acid in a concentration acid from about 5 ppm and 10 ppm and 2,4,5-trichlorophenoxyacetic acid in a concentration acid from about 5 ppm and 10 ppm; and (b) incubating the immature somatic embryo isolated from step (a) on a maturation medium for a length of time sufficient to reduce the water content of the somatic embryo by an amount effective to bring about an increased conversion vigor, said maturation medium comprising 6% to about 12% sucrose to foster development of said the immature somatic embryos into mature somatic embryos possessing well-formed cotyledons and radicle.

19. A method of producing seeds from multiple whole fertile plants, said method comprising the steps of:

(a) culturing aseptic cotyledonary tissue on a culturing media to form immature somatic embryos, said aseptic cotyledonary tissue being of Glycine max or Glycine soja or hybrid thereof, in the form of whole zygotic embryo with cotyledons 4 to 8 mm in length for Glycine max or hybrid and 1 to 4 mm in length for Glycine soja or in the form of cotyledons excised from said embryo or from derivation product of said cotyledonary tissue, said culture media comprising a combination of a first and second synthetic auxin in a concentration of about 20 to about 40 ppm, said said first synthetic auxin being selected from the group consisting of
2,4,5-trichlorophenoxyacetic acid,
para-chlorophenoxyacetic acid,
2-methyl-4-chlorophenoxyacetic acid, and
2,4-dichlorophenoxyacetic acid, and said second synthetic auxin being selected from the group consisting of indolebutyric acid and $\alpha$-naphthaleneacetic acid; and (b) incubating the immature somatic embryo isolated therefrom from step (a) on a maturation medium for a length of time sufficient to reduce the water content of the somatic embryo by an amount effective to bring about an increased conversion vigor, said maturation medium comprising 6% to about 12% sucrose to foster development of said the immature somatic embryos into mature somatic embryos possessing well-formed cotyledons and radicle.

20. A method of producing seeds from multiple whole fertile pants, said method comprising the steps of:

(a) culturing aseptic cotyledonary tissue on a culturing media to form immature somatic embryos, said aseptic cotyledonary tissue being of Glycine max or Glycine soja or hybrid thereof, in the form of whole zygotic embryo with cotyledons 4 to 8 mm in length for Glycine max or hybrid and 1 to 4 mm in length for Glycine soja or in the form of cotyledons excised from said embryo or from derivation product of said cotyledonary tissue, said culture media comprising a synthetic auxin in a concentration of from about 20 to about 40 ppm, said synthetic auxin being selected from the group consisting of
2,4,5-trichlorophenoxyacetic acid, para-chlorophenoxyacetic acid,
2- methyl-4-chlorophenoxyacetic acid, and
2,4-dichlorophenoxyacetic acid;

(b) removing the immature somatic embryo from the cotyledenary tissue; and (c) subculturing at least once the immature somatic embryo isolated from step (b) on media having the same components as set forth in step (a); and (d) incubating the immature somatic embryo isolated from step (c) on a maturation medium for a length of time sufficient to reduce the water content of the somatic embryo by an amount effective to bring about an increased conversion vigor, said maturation medium comprising a carbon source 6% to about 12% sucrose to foster development of said the immature somatic embryos into mature somatic embryos possessing well-formed cotyledons and radicle.

21. The method of claim 20, comprising the further step of incubating the immature somatic embryo isolated from step (c) on a maturation medium for a length of time sufficient to reduce the water content of the somatic embryo by an amount effective to bring about an increased conversion vigor, said maturation medium comprising 6% to about 12% sucrose to foster development of said the immature somatic embryos into mature somatic embryos possessing well-formed cotyledons and radicle.

22. A method of producing seeds from multiple whole fertile plants, said method comprising the steps of:

(a) culturing aseptic cotyledonary tissue on a culturing media to form immature somatic embryos, said aseptic cotyledonary tissue being of Glycine max or glycine soja or hybrid thereof, in the form of whole zygotic embryo with cotyledons 4 to [mm in length for Glycine max or hybrid and 1 to 4 mm in length for Glycine soja or in the form of cotyledons excised from said embryo or from derivation product of said cotyledonary tissue, said culture media comprising 2,4-dichlorophenoxyacetic acid in a concentration of from about 10 to about 40 ppm;

(b) removing the immature somatic embryo from the cotyledenary tissue; and (c) subculturing at least once the immature somatic embryo isolated from step (b) on media having the same components as set forth in step (a); and (d) incubating the immature somatic embryo isolated from step (c) on a maturation medium for a length of time sufficient to reduce the water content of the somatic embryo by an amount effective to bring about an increased conversion vigor, said maturation medium comprising a carbon source 6% to about 12% sucrose to foster development of said the immature somatic embryos into mature somatic embryos possessing well-formed cotyledons and radicle.

23. The method of claim 22, comprising the further step of incubating the immature somatic embryo isolated from step (c) on a maturation medium for a length of time sufficient to reduce the water content of the somatic embryo by an amount effective to bring about an increased conversion vigor, said maturation medium comprising 6% to about 12% sucrose to foster development of said the immature somatic embryos into mature somatic embryos possessing well-formed cotyledons and radicle.

* * * * *

UNITED STATES PATENT AND TRADEMARK OFFICE
CERTIFICATE OF CORRECTION

PATENT NO. : 5,008,200
DATED : April 16, 1991
INVENTOR(S) : Ranch et al.

It is certified that error appears in the above-indentified patent and that said Letters Patent is hereby corrected as shown below:

On the title page and column 1, lines 1-3, left column: Title should read:

--[54] PROPAGATING MULTIPLE WHOLE FERTILE PLANTS FROM IMMATURE LEGUMINOUS TISSUE--

<u>Cover page, left column:</u>     Related U.S. Application Data should read:

--[63] Continuation-in-part of Ser. No. 860,979, May 8, 1986, abandoned.--

Signed and Sealed this

Seventh Day of July, 1998

Attest:

BRUCE LEHMAN

*Attesting Officer*     *Commissioner of Patents and Trademarks*